(12) United States Patent
Diehl

(10) Patent No.: US 7,468,195 B2
(45) Date of Patent: Dec. 23, 2008

(54) SKIN TREATMENT PREPARATION

(75) Inventor: Christian Diehl, Bourg en Bresse (FR)

(73) Assignee: Crawford Healthcare Limited, Goostrey (GB)

( * ) Notice: Subject to any disclaimer, the term of this patent is extended or adjusted under 35 U.S.C. 154(b) by 0 days.

(21) Appl. No.: 11/744,731

(22) Filed: May 4, 2007

(65) Prior Publication Data

US 2007/0218045 A1 Sep. 20, 2007

Related U.S. Application Data

(63) Continuation-in-part of application No. 10/311,148, filed as application No. PCT/FR00/01601 on Jun. 9, 2000, now abandoned.

(51) Int. Cl.
*A61K 8/02* (2006.01)
*A61K 9/14* (2006.01)
*A61K 9/127* (2006.01)
*A61K 38/44* (2006.01)
*A61K 38/54* (2006.01)

(52) U.S. Cl. ............... 424/450; 424/401; 424/489; 514/62; 514/801

(58) Field of Classification Search ......... 424/401, 424/450, 489, 94.2, 94.4; 514/62, 801
See application file for complete search history.

(56) References Cited

U.S. PATENT DOCUMENTS

| 4,217,344 | A |   | 8/1980 | Vanlerberghe et al. |   |
|---|---|---|---|---|---|
| 5,554,374 | A | * | 9/1996 | Olivier-Terras | 424/401 |
| 5,616,323 | A | * | 4/1997 | Ginoux et al. | 424/758 |
| 5,622,656 | A |   | 4/1997 | Huc et al. |   |
| 5,747,043 | A |   | 5/1998 | Ginoux et al. |   |
| 6,048,886 | A | * | 4/2000 | Neigut | 514/412 |
| 6,235,272 | B1 |   | 5/2001 | Greene |   |

FOREIGN PATENT DOCUMENTS

| FR | 2315991 | 6/1975 |
| FR | 2642329 | 1/1989 |
| FR | 2716884 | 3/1994 |
| JP | A 4-29915 | 1/1992 |

* cited by examiner

*Primary Examiner*—Johann R Richter
*Assistant Examiner*—Konata M George
(74) *Attorney, Agent, or Firm*—Oliff & Berridge, PLC

(57) ABSTRACT

A skin treatment preparation including carriers, a medicinal vector encapsulating a plant extract (Cucumis melo protein extract) rich in reductase, catalase and superoxide dismutase is characterized in that the medicinal vector, of nanospheres, represents 1 to 20 wt. % of the weight of the preparation; and the encapsulated plant extract represents 5 to 15 wt. % of the weight of the nanospheres; and the encapsulated plant extract may have the following enzymatic concentrations: reductase between 100 and 1000 IU, catalase between 100 and 1000 IU, and superoxide dismutase between 500 and 5000 IU. The preparation is useful for limiting depigmentation and reducing inflammatory front in vilitigo pathology and possible repigmentation.

9 Claims, No Drawings

SKIN TREATMENT PREPARATION

CROSS-REFERENCE TO RELATED APPLICATION

This application is a continuation-in-part of U.S. patent application Ser. No. 10/311,148, filed Apr. 9, 2003, which is a U.S. National Stage Application of PCT/FR00/01601, filed Jun. 9, 2000, each of which are incorporated herein by reference in their entireties.

BACKGROUND

The invention relates to a novel skin treatment preparation formed by a mixture of excipients, plant compounds containing enzymes and medicinal vectors, intended for preventing or stopping the development of the inflammatory front during the progressive phases of vitiligo and possible repigmentation.

As is known, the expression "medicinal vectors" denotes small, hollow particles which form reservoirs for active products which are thus protected and which can be released or discharged when the time comes at the most suitable site (bioavailability). Liposomes, described, for example, in document French Patent No. 2,315,991 corresponding to document U.S. Pat. No. 4,217,344, are the most well-known of these vectors.

SUMMARY

Recently, studies by research scientists have made it possible, based on fundamental research, to obtain a better understanding of vitiligo, and to indicate novel therapeutic directions.

They examined the autosomal theory of vitiligo, according to the following sequence: thioredoxin reductase, a thionenzyme present in human keratinocytes and melanocytes, reduces free radicals, thus possibly providing the first line of defense against the damage inflicted on the skin by free radicals generated by UV radiation. Moreover, the superoxide anion radical has been shown to be the true substrate for tyrosinase, preferably with molecular oxygen.

A low level of catalase has been reported in both lesional and nonlesional epidermis of patients suffering from vitiligo, compared to controls free of this disease.

It was then suggested that these low levels of catalase could lead to a higher concentration of hydrogen peroxide in these patients. This increase in the level of $H_2O_2$ might induce depigmentation and destroy the melanocytes, and might also maintain low levels of catalase, $H_2O_2$ being able to inhibit the hematological center of the catalase.

Hydrogen peroxide can act as a reversible inhibitor of tyrosinase. It induces a photochemical reduction reaction, producing highly reactive hydroxyl ions and radicals. These are capable of decoloring physiological melanin, and of inducing melanocyte membrane lysis.

The same research scientists have also demonstrated an increase in TNF-alpha, GTP, 6-BH4 and PAH in the epidermis after exposure to UV radiation.

Through the recent use of Raman spectroscopy, they have been able to demonstrate, for the first time, the high levels of $H_2O_2$ in the epidermis of patients suffering from vitiligo.

Recent studies carried out on cell cultures of human melanocytes taken from affected patients, treated with a plant extract rich in reductase, catalase and superoxide dismutase, have indisputably shown the decrease in the level of hydrogen peroxide on the treated cells, and also a receding of the inflammatory phenomenon associated with vitiligo.

These investigations therefore lead to the notion that a skin preparation containing these plant extracts, included in medicinal vectors making it possible to protect them and ensuring preferential release thereof at the site of keratinocytes and melanocytes, would reduce the inflammatory profile associated with vitiligo in a satisfactory manner, and should therefore limit, or even stop, the skin depigmentation.

The invention is therefore directed toward creating an improved preparation of the type in question with *Cucumis melo* protein extract, which gives the best possible results in terms of limiting, or even stopping, skin depigmentation, which is easy to produce, stable and economical, and exhibits no inopportune effects of release.

DETAILED DESCRIPTION OF EMBODIMENTS

This skin treatment preparation, comprising excipients and a medicinal vector encapsulating a plant extract rich in reductase, catalase and superoxide dismutase, is characterized:

in that the medicinal vector, consisting of nanospheres encapsulating a plant extract rich in reductase, catalase and superoxide dismutase, represents between 1% and 20% of the weight of the preparation, and in that the plant extract used is rich in reductase, catalase and superoxide dismutase.

In embodiments, plant extracts may include *Cucumis melo* protein extract and/or other protein extracts obtainable from most melons, such as described in U.S. Pat. No. 5,747,043, incorporated herein by reference in its entirety.

The term "nanospheres" denotes medicinal vectors, consisting of particles, generally spherical or ovoid, of nanometric size, encapsulating a given substance, in this case a plant extract rich in reductase, catalase and superoxide dismutase. These vectors are widely described in the literature.

In other words, the invention lies in a double selection, namely, first of all, the selection of a specific vector, namely nanospheres encapsulating a specific active agent, a plant extract rich in reductase, catalase and superoxide dismutase.

It could not be imagined that this double selection would make it possible to successfully solve the problem posed, namely, by virtue of the small size of the nanospheres, better penetration as far as the keratinocytes and melanocytes and therefore better bioavailability of the active agents at this stage and, in addition, by virtue of the choice of with a balanced content of reductase, catalase and superoxide dismutase, a satisfactory efficiency as regards limiting, or even stopping, skin depigmentation.

Advantageously, in practice:

the nanospheres are hollow spheres comprising a membrane made of collagen and glycosaminoglycans, such as those marketed by COLETICA under the registered trade marks NANOTHALASPHERE and NANOCOLLASPHERES; these nanospheres are described in document FR-A-8901221; this type of vector has the advantage, in combination with excipients, of giving skin preparations which are less irritant, completely biodegradable, biocompatible and release in a controlled manner;

the nanospheres loaded with plant extract rich in reductase, catalase and superoxide dismutase represent between 1% and 20% of the weight of the preparation, preferably between 3 and 12%; specifically, it has been observed that, if the proportion of nanospheres is less than 1%, virtually no limitation of depigmentation is obtained, and that, on the other hand, when this proportion exceeds 20%, release is excessive and liable to harm the normal physiological mechanisms of the skin.

The plant extract load of the nanospheres represents from 5 to 15% of the weight of these nanospheres; specifically, it has been observed that a load of less than 5% gives irregular results on the limitation of skin depigmentation, and possible repigmentation, whereas a load of greater than 15% is not industrially acceptable with regard to the production of the nanospheres; that said, the best results are obtained with a proportion close to 10%.

The plant extract selected should have the following enzyme concentrations;

reductase: between 100 and 1000 IU
catalase: between 100 and 1000 IU
superoxide dismutase: between 500 and 5000 IU.

Specifically, enzyme concentrations of less than 100 IU for reductase and catalase and 500 IU for superoxide dismutase provide a relatively unsatisfactory effectiveness, whereas concentrations of greater than 1000 IU for reductase and catalase and greater than 5000 IU for superoxide dismutase are hardly compatible with the physiological demands of human skin; that said, the best results were obtained with the following enzyme concentrations:

reductase: 500 IU
catalase: 500 IU
superoxide dismutase: 1000 IU

Generally, the Cucumis melo protein extracts have an improved superoxide dismutase activity and possibly also improved catalase activity compared with known protein extracts obtained from most melons. The extracts result from a selection from a large number of melons. In embodiments, the plant extract may be obtained from climacteric fruits such as melon (*Cucumis melo*) having superoxide dismutase activities of the order of 22 to 24 enzyme units per mg of proteins and a catalase activity of the order of 35 to 40 enzyme units per mg of proteins. The plant extract may have a superoxide dismutase enzyme activity greater than 30 enzyme units per mg of proteins as well as a catalase enzyme activity greater than 45 enzyme units per mg of proteins. Additionally, the *Cucumis melo* protein extract may have a superoxide dismutase enzyme activity greater than 50 enzyme units per mg and possibly a catalase enzyme activity greater than 60 enzyme units per mg of proteins.

The preparation also contains excipients commonly used for such a skin application.

These excipients should not affect the stability of the nanoparticles, nor interact with them or with one another. It is therefore preferable for the proportion of fatty substances to be as low as possible, and in particular less than half, or even less than a third. Usually, the mixture of excipients may also contain antioxidants and/or preservatives known for such a preparation.

In a practical embodiment, the preparation according to the invention comprises:

10% of nanospheres encapsulating the Cucumis melo protein extract (hereinafter "plant active agent");
1% of preservative; and
the remainder up to 100% consisting of demineralized water and a mixture of excipients commonly used for a skin application.

It goes without saying that, in the preparation according to the invention, it is essential that the nanospheres encapsulating the plant extract and the excipients do not react with one another.

Generally, the finished preparation is very light in color, even light beige, depending on the quality of the fatty substances which are used. This preparation is creamy, smooth, easy to spread, and can be readily conserved at ambient temperature, in particular in an airless tube, even for more than a year.

This skin preparation is easily applied by hand, and penetrates rapidly under the effect of slight massaging. Good results are obtained by applying this preparation twice a day for one to five months, or even continuously. Once the preparation has been applied to the skin, the nanospheres encapsulating the plant extract penetrate into the stratum corneum and come into contact with the keratinocytes and melanocytes. The two membranes then fuse, which allows the plant extract to pass into the cytoplasm of the keratinocyte and of the melanocyte, entraining therein the reductase, catalase and superoxide dismutase which it contains.

There ensues a chemical reaction comprising reduction of the hydrogen peroxide which is located therein in an excessive amount, and a small loss, or even no loss, of melanin. There ensues a limitation, or even an arrest, of the depigmentation associated with vitiligo, and possibly repigmentation. There also ensues a decrease, or even a disappearance, of the inflammatory front very often associated with the depigmentations, these being phenomena which could not be obtained until now.

The manner in which the invention can be produced and the advantages which ensue therefrom will emerge more clearly from the examples of preparation which follow.

EXAMPLE 1

The following respectively are mixed at ambient temperature, and with gentle agitation, in 220 grams (22%) of demineralized water:

3 grams (0.30%) of a gelling agent based on modified cellulose marketed by GOODRICH under the brand name "CARBOPOL 934";

30 grams (3%) of nanospheres encapsulating *Cucumis melo* protein extract rich in reductase, catalase and superoxide dismutase, provided in the form of an aqueous suspension marketed by COLETICA under the brand name "NANOTHALASPHERES", and the membrane of which is made of collagen and glycosaminoglycans; these nanospheres are presented as being microcapsules with a diameter of less than one (1) micrometer, characterized in that they comprise a mixed wall of marine collagen or atelocollagen, and of crosslinked glycosaminoglycans, the proportion of glycosaminoglycans relative to the marine collagen or to the atelocollagen possibly ranging from 15% to 50% by weight; the glycosaminoglycans are chosen from the group consisting of chondroitin 4-sulfate, chondroitin 6-sulfate, dermatan sulfate, heparin sulfate, keratan sulfate and eparin and its derivatives;

10 grams (1%) of a liquid preservative based on propylene glycol, on diazolidinylurea, on methylparaben and on propyparaben, marketed by SUTTON under the brand name "GERMABEN II";

1 gram (0.1%) of an ion-chelating agent, known as disodium EDTA; and agitation is carried out slowly at ambient temperature, until a completely homogeneous mixture is obtained.

Separately, with rapid agitation (1000 rpm) and at 80° C., the following are mixed in order:

10 grams (1%) of an excipient based on cetyl alcohol;
90 grams (9%) of another excipient, based on 2 octyldodecyl myristate;

80 grams (8%) of an excipient based on a nonionic derivative of white beeswax, marketed by GATTEFOSSE under the brand name "APIFIL"; and 80 grams (8%) of an excipient based on isostearyl isostearate.

The mixture is agitated rapidly until complete homogenization is obtained. Demineralized water, heated to 82° C., is then added to the latter mixture, in a proportion of 456.5 grams (45.65%). To initiate the emulsion, rapid agitation is carried out while pouring this water into the mixture. When the emulsion is formed, and when the temperature has come back to 30-35° C., the first phase containing the nanospheres of plant active agent are then added, and then 6 grams (0.6%) of a 50% triethanolamine solution are added, in order to adjust the pH, followed by 3 grams (0.3%) of a fragrance and, finally, 0.5 gram (0.05%) of an antioxidant marketed by GATTEFOSSE under the reference "WL 774". The entire combination is mixed slowly at 30-35° C.

The preparation obtained is an emulsion of the oil-in-water type, which is white-light beige (depending on the quality of the fatty substances used) in color, smooth, creamy and semi-liquid, and the pH of which is between 5 and 7.5. Its sui generi odor is linked to the fragrance used.

This preparation, which is stable over time (no inopportune release after a year of storage) can be applied to the skin at a rate of two applications per day for an unlimited period.

Limitation, or even an arrest, of the skin depigmentation associated with vitiligo, and possible repigmentation, are obtained, sometimes as soon as the third week, more generally within five months, following the commencement of application.

In addition, application of this emulsion appears to prevent further depigmentations.

EXAMPLE 2

Example 1 is repeated, removing the nanosphere encapsulating the plant extract. No effect is observed.

EXAMPLE 3

Example 1 is repeated, replacing the nanospheres with commercial liposomes encapsulating the plant extract.

An emulsion is obtained which has substantially the same appearance and the same physical properties as in example 1. However, the limitation of the depigmentation which is observed is slower and more spasmodic than in example 1.

EXAMPLE 4

Example 1 is repeated, replacing the plant extract chosen with another plant extract which contains neither reductase, nor catalase, nor superoxide dismutase. No result is observed.

These examples clearly show the activity associated with the effect of synergy resulting from the combination of the nanospheres encapsulating a plant extract rich in reductase, catalase and superoxide dismutase on the limitation of depigmentation and the reduction of the inflammatory front during the process of development of vitiligo, and possible repigmentation.

In this way, these skin preparations can be used successfully in patients exhibiting a progressive vitiligo pathology.

What is claimed is:

1. A skin treatment preparation, comprising excipients and a medicinal vector encapsulating a *Cucumis melo* protein extract rich in reductase, catalase and superoxide dismutase, wherein:
    the medicinal vector consists of nanospheres and represents between 1% and 20% of the weight of the preparation; and
    the nanospheres in the form of spherical particles encapsulating the *Cucumis melo* protein extract have a membrane made of collagen and glycosaminoglycan, wherein a load of the *Cucumis melo* protein extract of the nanospheres is from 5 to 15 weight percent of the nanospheres.

2. The skin treatment preparation according to claim 1, wherein the *Cucumis melo* protein extract has the following enzyme concentrations:
    reductase: between 100 RI and 1000RI;
    catalase: between 100 IU and 1000 IU; and
    superoxide dismutase: between 500 IU and 5000 IU.

3. The skin treatment preparation according to claim 1, wherein the excipients contain a mixture of oils, fatty acids, antioxidants and preservatives.

4. A skin treatment preparation comprising excipients and medicinal vectors encapsulating a *Cucumis melo* protein extract rich in reductase, catalase and superoxide dismutase according to claim 1, wherein the skin treatment preparation contains, per hundred parts:
    1 to 20% of nanospheres encapsulating the *Cucumis melo* protein extract;
    b 1% of preservative;
    0.1% of an ion-chelating agent;
    0.3% of a gelling agent based on modified cellulose;
    0.6% of an agent for adjusting the pH; and
    the remainder up to 100% consisting of demineralized water and a mixture of excipients commonly used for a skin application.

5. The skin treatment preparation according to claim 4, wherein the skin treatment preparation contains 3% of nanospheres encapsulating the *Cucumis melo* protein extract.

6. A method for treating vitiligo in skin of a human, the method including:
    providing a skin treatment preparation, wherein the skin preparation comprises excipients, a medicinal vector encapsulating a plant extract rich in reductase, catalase and superoxide dismutase, wherein the medicinal vector consists of nanospheres and represents between 1 and 20 weight percent of the skin preparation, and wherein the nanospheres in a form of spherical particles encapsulating the plant extract have a membrane made of collagen and glycosaminoglycan; and
    applying the skin treatment preparation to the skin of the human having vitiligo1 wherein a load of the Cucumis melo protein extract of the nanospheres is from 5 to 15 weight percent of the nanospheres.

7. The method according to claim 6, wherein the excipients contain a mixture of oils, and fatty acids, antioxidants and preservatives.

8. The method according to claim 6, wherein the plant extract has the following enzyme concentrations:
    reductase: between 100 IU and 1000 RI;
    catalase: between 100 IU and 1000 IU; and
    superoxide dismutase: between 500 IU and 5000 IU.

9. The method according to claim 6, wherein the plant extract is a *Cucumis melo* protein extract.

* * * * *